US006573254B1

(12) United States Patent
Kuenzel et al.

(10) Patent No.: US 6,573,254 B1
(45) Date of Patent: Jun. 3, 2003

(54) METHOD FOR THE STIMULATION OF SPERM PRODUCTION AND GONADAL DEVELOPMENT IN ANIMALS

(75) Inventors: Wayne J. Kuenzel, University Park, MD (US); John D. Kirby, Prairie Grove, AR (US)

(73) Assignees: University of Maryland, College Park, MD (US); University of Arkansas, Fayetteville, AR (US)

( * ) Notice: Subject to any disclaimer, the term of this patent is extended or adjusted under 35 U.S.C. 154(b) by 0 days.

(21) Appl. No.: 09/555,383

(22) PCT Filed: Feb. 3, 1999

(86) PCT No.: PCT/US99/02520

§ 371 (c)(1), (2), (4) Date: May 30, 2000

(87) PCT Pub. No.: WO99/38376

PCT Pub. Date: Aug. 5, 1999

Related U.S. Application Data

(60) Provisional application No. 60/073,550, filed on Feb. 3, 1998.

(51) Int. Cl.[7] .................... A61K 31/655; A61K 31/505

(52) U.S. Cl. ....................................... 514/157; 514/274

(58) Field of Search ................................ 514/157, 274; 426/635

(56) References Cited

U.S. PATENT DOCUMENTS

| | | | |
|---|---|---|---|
| 2,218,490 A | 10/1940 | Winnek | 260/556 |
| 2,240,496 A | 5/1941 | Dvornikoff | 260/397.7 |
| 2,411,495 A | 11/1946 | Dohrn et al. | 260/397.7 |
| 2,417,005 A | 3/1947 | Martin et al. | 260/397.7 |
| 2,712,012 A | 6/1955 | Clark | 260/239.7 |
| 2,790,798 A | 4/1957 | Lester et al. | 260/239.7 |
| 2,888,455 A | 5/1959 | Kano et al. | 260/239.9 |
| 3,098,069 A | 7/1963 | Camerino et al. | 260/239.7 |
| 3,127,398 A | 3/1964 | Bretschneider et al. | 260/239.75 |
| 3,132,139 A | 5/1964 | Bretschneider et al. | 260/239.75 |
| 3,214,335 A | 10/1965 | Diedrich | 167/51.5 |
| 3,375,247 A | 3/1968 | Doub et al. | 260/239.75 |
| 3,562,258 A | 2/1971 | Loop et al. | 260/239.9 |
| 4,151,164 A | 4/1979 | Menzl et al. | 260/239.95 |
| 4,780,451 A | 10/1988 | Donaldson | 514/12 |
| 5,162,306 A | 11/1992 | Donaldson | 514/12 |

OTHER PUBLICATIONS

Knowlton et al., Effects of Transient Treatment with 6–N–Propyl–2–Thiouracil on Testis Development an Functio in Breeder Turkeys, Feb. 1999 Poultry Science, 78:999–1005.*

Kuenzel et al., Sulfamehtazine Advances Puberty in Chicks via a Reduction in Thyroid Hormone (T3) Followed by a Central or Pituitary Mediation of Gonadotropins, Aug. 1995 Poultry Science Association Annual Meeting Abstracts, 74 Supp.1 102.*

(List continued on next page.)

*Primary Examiner*—Russell Travers
*Assistant Examiner*—Shengjum Wang
(74) *Attorney, Agent, or Firm*—Sterne, Kessler, Goldstein & Fox P.L.L.C.

(57) ABSTRACT

Disclosed is a method to stimulate or enhance sperm development in males and gonadal development in females by administration of an agent which results in a transiently level of a thyroid hormone such as $T_3$ and increased gonadotropin levels in the blood.

18 Claims, 7 Drawing Sheets

OTHER PUBLICATIONS

Ban Tienhoben et al., The Effect of Sulfamethazine Feeding on the Thyroids, Combs and Testes of Single Comb Whtie Leghorn Cockerels, Jan. 1956 Poultry Science, 35:179–191.*

Kirby et al., Effects of Transient Prepubertal 6–N–Propyl–2–Thoiuracil on Testis Development and Functio in the Domestic Fowl, Jun. 1996 Biology of Reproduction, 55:910–916.*

Mayer, Inhibition of Thyroid Function in Beagle Puppies by Popylthiouracil without Disturbance of Growth or Health, Jun. 1947 Endocrinology, 40:165–181.*

Jannini et al., Thyroid Hormone and Male Gonadal Function, 1995 Endocrine Reviews 16:443–459.*

Kuenzel et al. (1996), "Evidence that stimulation of gonadal development . . . ", Poultry Science, vol. 75 supp. 1, p. 93.*

Kuenzel et al. (1997), "Neuroendocrine control of early sexual development", Perspectives in Avian Endocrinology, pp. 81–90.*

Vizcarra et al., Rescue of inpaired spermatogenesis . . . , Biology of Reproduction, 1998 vol. 58 supp. 1, p. 104.* van Tienhoven et al., "The effects of sulfamehtazine feeding on the thyroids . . . ", Poultry Science, 1956 vol. 35 No. 1, pp. 179–191.*

Donaldson, L.E., "Production of super–ovulation in cattle and other farm animals—by administration of follicle stimulating hormone with minor proportion of luteinising hormone," Database WPIDS, London: Derwent Publications Ltd., Accession No. 92–398060/48, Derwent WPI abstract for New Zealand patent No. 227166 A.

du Souich, P. et al., "Effect of aminoglycosides on the disposition of thyroid hormones and thyroglobuin," *Clin. Pharmacol. Ther. 38*:686–691, C.V. Mosby Company (1985).

Fraley, G.S., and Kuenzel, W.J., "Precocious Puberty in Chicks (*Gallus domesticus*) Induced by Central Injections of Neuropeptide Y," *Life Sci. 52*:1649–1656, Pergamon Press (1993).

Kalra, S.P. et al., "Hypothalamic Neuropeptide Y: a Circuit in the Regulation of Gonadotropin Secretion and Feeding Behavior," *Ann. NY Acad. Sci. 611*:273–283, The New York Academy of Sciences (1990).

Kirby, J.D., and Hess, R.A., "Increasing Testis Size and Sperm Production in the Fowl," NRI Competitive Grant, Accession No.: 0169551, Subfile: CRIS, United States Department of Agriculture (visited Feb. 23, 2001), <http://cris.csrees.usda.gov/cgi–bin/starfinder/16920/crisassist.txt> (1995).

Kiser, J. S. et al., "Treatment of Experimental and Naturally Occurring Fowl Cholera with Sulfamethazine," *Poult. Sci. 27*:257–262, Poultry Science Association (1948).

Kuenzel, W.J., and van Tienhoven, A., "Nomenclature and Location of Avian Hypothalamic Nuclei and Associated Circumventricular Organs," *J. Comp. Neurol. 206*:293–313, Alan R. Liss, Inc. (1982).

Kuenzel, W.J. et al., "A Comparison of Precocious Puberty Produced in Male Chicks by Sulfamethazine and Hypothalamic Knifecuts," *Poult. Sci. 72* (*Suppl. 1*):96, Abstract No. 286, Poultry Science Association, Inc. (1993).

Kuenzel, W.J. et al., "Increased Levels of Neuropeptide Y (NPY) and Dopamine (DA) in the Median Eminence of Chicks Showing Early Gonadal Development," *Society for Neurosci. 20*:996, Abstract No. 409.2, Society for Neuroscience (1994).

The Merck Index, Twelfth Edition, pp. 1523–1524, Entry 9083, "Sulfamethazine," Merck Reseach Laboratories, Whitehouse Station, NJ (1996).

Sar, M. et al., "Localization of Neuropeptide–Y Immunoreactivity in Estradiol–Concentrating Cells in the Hypothalamus," *Endocrinology 127*:2752–2756, The Endocrine Society (1990).

van Tienhoven A. et al., "The Effect of Sulfamethazein Feeding on the Thyroids, Combs and Testes of Single Comb White Leghorn Cockerels," *Poult. Sci. 35*:179–191, Poultry Science Association (1956).

Vizcarra, J.A. et al., "Rescue of Impaired Spermatogenesis in Adult Male Fowl Following Unrestricted Prepubertal Growth and Subsequent Growth Restriction," *Biol. Reprod. 58* (*Suppl. 1*):104, Abstract No. 105, Society for the Study of Reproduction (1998).

Walsh, K.M., and Kuenzel, W.J., "Effect of Sulfamethazine on Sexual Precocity and Neuropeptide Y Neurons Within the Tuberoinfundibular Region of the Chick Brain," *Brain Res. Bull. 44*:707–713, Elsevier Science Inc. (1997).

International Search Report for International Application No. PCT/US99/02520, mailed May 12, 1999.

Kuenzel, W.J. et al., "Early Sexual Maturation Induced by Sulfamethazine in Chicks is Mediated by Elevated LH and FSH Release and Transient Inhibition of Thyroid Hormones," *Poult. Sci. 74* (*Suppl. 1*):75, Abstract No. 223, Poultry Science Association, Inc. (1995).

Kuenzel, W.J. et al., "Sulfamethazine Advances Puberty in Chicks Via a Reduction in Thyroid Hormone($T_3$) Followed by a Central of Pituitary Mediation of Gonadotropins," *Soc. Neurosci. 21*:102, Abstract No. 46.13, Society for Neuroscience (1995).

Kuenzel, W.J. et al., "Neuroendocrine control of early sexual development," in *Perspectives in Avian Endocrinology*, Harvey, S. and R.J. Etches, eds., Journal of Endocrinilogy Limited, Bristol, UK, pp. 81–90 (1997).

* cited by examiner

FIG. 1
A. "METABOLIC"
B. "PHOTOPERIODIC"
GENETIC SELECTION PHASE
FEED RESTRICTION PHASE
PHOTOSTIMULATION PHASE
PHOTOPERIOD:
LD 24:0
LD 23:1
LD 8:16
LD 12:12 TO LD 16:8
DAYS:
1 2 3
49
50
140
141
182
WEEKS:
7 wks
20 wks
26 wks
DIET:
STARTER
GROWER
GROWER
MANAGEMENT:
AD LIBITUM
MARKED FEED RESTRICTION
SOME FEED RESTRICTION

METHOD FOR THE STIMULATION OF SPERM PRODUCTION AND GONADAL DEVELOPMENT IN ANIMALS

CROSS REFERENCE TO RELATED APPLICATIONS

The present application is a 371 of PCT/US99/02520, filed Feb. 3, 1999, which claims priority to U.S. application No. 60/073,550, filed Feb. 3, 1998, the contents of which are fully incorporated by reference herein.

BACKGROUND OF THE INVENTION

1. Field of the Invention

The invention relates to method of enhancing gonadal development in an animal by administration of an agent which results in lowered levels of a thyroid hormone such as $T_3$ and elevation of plasma gonadotropins (luteinizing hormone (LH) and follicle stimulating hormone (FSH)).

2. Related Art

Over the past few decades two environmental manipulations have been used in the poultry industry to regulate the onset of sexual maturation: photoperiod and nutrition. Pullets kept in total darkness or under short photoperiods display a delay in initial egg production (Wilson and Woodward, *Poultry Sci.* 37:1054–1057 (1958); King, *Poultry Sci.* 40:479–484 (1961)). In contrast, increasing day lengths have been shown to stimulate reproductive development in many avian species including domestic fowl (Farner and Follett, *J. Anim. Sci.* 25:Suppl. 90–118 (1966); van Tienhoven and Planck, The effect of light on avian reproductive activity, Handbook of Physiology, Endocrinology II, Part 1, Chapter 4, pp. 79–107 1972). Chicks can be maintained at a physiological age of about 10 days for many months using protein-, amino acid-, or energy-deficient diets just sufficient to fill maintenance requirements (McCance, *Br. J. Nutr.* 14:59–73 (1960); Dickerson and McCance, *Br. J. Nutr.* 14:331–338 (1960)). Return to an unrestricted, nutritional diet restores growth and development to a normal rate with little subsequent effect on adult body size or egg production (McRoberts, *J. Nutr.* 87:31–40 (1965)).

Continued manipulation of photoperiod and nutrition (particularly feed restriction) has been used in the broiler industry. The latter has become a necessary management tool due to a propensity for broiler-breeders to become obese. This is a consequence of the marked improvements in weight gain and feed conversion made by genetic selection and advances in the knowledge of dietary requirements. Unfortunately, rapid growth rate in broilers has resulted in obesity and decreased efficiency in the reproductive system of breeder stock (Reddy, Artificial insemination of broilers: economic and management implications. In:Proceedings of the First International Symposium on the Artificial Insemination of Poultry. The Poultry Science Assoc., Inc., Savoy, Ill., pp.73–89, 1994). Research has been completed comparing the reproductive performance of females between broiler breeder and egg-laying strains of domestic chickens (Dunn and Sharp, *J. Reprod. Fert.* 90:329–335 (1990); Eitan and Soller, *Poultry Sci.* 70:2017–2022 (1991); *Poultry Sci.* 73:769–780 (1994); *Poultry Sci.* 75:828–832 (1996); Robinson, Ovarian form and function in chickens of varying reproductive status. Final Report, Alberta Agricultural Research Institute Project # AAR1920202. Univ. Alberta, Edmonton, Canada (1994); Eitan et al. *Poultry Sci.* 77:1593–1600 (1998)). Conclusions that have been reached from the cited studies are:

1. Female broilers compared to Leghorns are less responsive to photoperiodic manipulations with respect to optimal reproductive performance (Eitan and Soller, *Poultry Sci.* 70:2017–2022 (1991); *Poultry Sci.* 73:769–780 (1994); Eitan et. al. *Poultry Sci.* 77:1593–1600 (1998));
2. Layer and broiler females differ in the minimal number of hours of light required to stimulate release of gonadotropins and initial development of their reproductive systems [critical day length, (CDL)] and the minimal number of hours of light above which no further increase in release of gonadotropins occurs [saturation day length, (SDL)] (Dunn and Sharp, *J. Reprod. Fert.* 90:329–335 (1990); Eitan et al. *Poultry Sci.* 77:1593–1600 (1998)); and,
3. Broiler breeder hens are less responsive to artificially increased photoperiodic manipulations compared to table egg layers under the effects of feed restriction (Robinson, Ovarian form and function in chickens of varying reproductive status. Final Report, Alberta Agricultural Research Institute Project # AAR1920202. Univ. Alberta, Edmonton, Canada (1994); Eitan et al. *Poultry Sci.* 77:1593–1600 (1998)).

Eitan and Soller, *Poultry Sci.* 75:828–832 (1996), compared the performance of male broiler breeders to that of male Leghorn or layer-type poultry under controlled photoperiod and/or dietary manipulations. They developed a maturation index for comparing different lines of birds.

There are clear indications that the reproductive system of broiler breeders has been compromised, particularly during the past decade (Beaumont, et al. *Br. Poult. Sci.* 33:649–661 (1992); Reddy, Artificial insemination of broilers: economic and management implications. In:Proceedings of the First International Symposium on the Artificial Insemination of Poultry. The Poultry Science Assoc., Inc., Savoy, Ill., pp.73–89 (1994); Eitan and Soller, *Poultry Sci.* 75:828–832 (1996); Goerzen et al. *Poultry Sci.* 75:962–965 (1996)). Elite male broiler breeders have been shown to exhibit premature loss of adequate numbers of viable spermatozoa. It has been suggested that up to 80% of selected males in pure lines are lost due to significant decreases in semen production (Personal communication with primary breeder personnel in the broiler industry; unpublished data from over 200 male broiler breeders). This marked reduction of selection potential can dramatically reduce genetic progress that can be made within a given type of bird, reducing the future competitiveness of specific lines.

Sulfamethazine (SMZ) is an antibiotic developed by Merck in the late 1940s for treating fowl cholera (Kiser et al. *Poultry Sci.* 27:257–262 (1948)) as well as other poultry diseases, such as coccidiosis. A side effect associated with chronic use of SMZ is a marked red coloration of the comb and increased size of both comb and testes (van Tienhoven et al. *Poultry Sci.* 35:179–191 (1956)). Its mechanism of action in this regard is unknown. Further studies have been conducted with broiler chicks. The compound significantly increases testes development, transiently suppresses a thyroid hormone, increases plasma gonadotropins, appears to augment photoperiodic response, induces the hypothalamo-pituitary-gonadal axis, and increases the number of immuno-stained neuropeptide Y(NPY) neurons in the mediobasal hypothalamus and infundibular nucleus (IN) (Macko, Walsh and Kuenzel, *Brain Res. Bull.* 44:707–713 (1997); Kuenzel, Macko, Walsh and Proudman, In Perspectives in Avian Endocrinology (Eds. S. Harvey and R. J. Etches), Journal Endocrinology Ltd., Bristol, pages 81–90 (1997). In addition, it has been shown that intracerebroventricular (ICV) administration of NPY to chicks stimulates growth of the testes (Fraley and Kuenzel, *Life Sci.* 52:1649–1656 (1993)). In the rat, it has been shown that NPY neurons in the arcuate nucleus [the IN of the chick is equivalent to the arcuate n. (ARC) of mammals, (Kuenzel and van Tienhoven, *J. Comp. Neurol.* 206:292–313 (1982)), appear to be involved in augmenting the LH surge in females (Kaira and Crowley, *Ann. N.Y. Acad. Sci.* 611:273–283 (1984); Sar et al. *Endocrinology* 127:2752–2756 (1990)).

SUMMARY OF THE INVENTION

The invention relates to a method for enhancing the development of viable sperm in a male animal and ovarian development in a female animal, comprising administering to said animal an effective amount of an agent which transiently lowers the levels of a thyroid hormone, specifically $T_3$, e.g. by affecting its synthesis or metabolism, and which agent also increases gonadotropins. The most robust effect occurs in males. Normally, semen is not obtained from commercial poultry lines until 16–25 weeks of age. According to the present invention, semen production is produced by 9 weeks of age. Thus, the present invention represents a significant advance in the art.

The invention also relates to a method for synchronizing the onset of puberty in feed-restricted and light-restricted birds by administering to the birds the agent on or about the time that the photoperiod is increased (e.g. weeks 20 through 28 for broiler breeders). The invention also relates to a method for administrating the agent near the end of a bird's reproductive cycle to maintain and extend its reproductive productivity. All three applications of the invention result in a transient lowering of the level of a thyroid hormone and elevation of plasma gonadotropin levels.

The invention is also directed to a method of preparing the diets of the animals and their storage to ensure a uniform distribution and stability of the agent thereby effecting a uniform gonadal response by the animals consuming the rations.

The invention serves not only to bring animals earlier into the reproductive state. When coupled with photoperiodic manipulation, the agent can be withdrawn from the diet and the reproductive state can be maintained by photostimulation with a long, daily photoperiod.

In addition, the present invention overcomes the problem of early cessation of the reproductive systems of animals. In the poultry industry, some males exhibit a collapse of their reproductive system earlier than expected. The result is a significant decrease in the fertility of eggs produced by a particular flock. According to the present invention, an agent which results in reduced levels of a thyroid hormone and elevated gonadotropin blood levels can be administered to the animal to maintain or extend the length of the viable reproduction period.

The agent also stimulates gonadal development in female poultry. Thus, the invention also relates to a method for stimulating development of the ovary of female poultry, comprising administering to said poultry an effective amount of the agent. The invention also relates to a method for maintaining egg production of female poultry for a period of time longer than usual, comprising administering to said poultry an effective amount of the agent near the end of the reproductive stage of their life cycle.

A common practice in the poultry industry is to recycle birds for a second season. This involves inducing a molt which in turn causes regression of the gonads. The agent can be used to bring birds back into a reproductive state sooner. In addition, the agent can be used at the end of the second reproductive cycle to sustain their productivity for a longer period of time. Thus, in a method to recycle birds for a second season involving inducing a molt whereby regression of the gonads occurs, the invention also relates to the improvement comprising administering to the birds an effective amount of the agent, whereby the birds are brought back into a reproductive state sooner. The invention also relates to a method to sustain the reproductive productivity of recycled birds at the end of their second reproductive cycle, comprising administering to the birds an effective amount of the agent. The invention is not limited to chickens and has beneficial effects in turkeys, quail, guinea fowl, ducks, game birds and other avian species.

In addition to stimulating gonadal development, the compound likewise stimulates song in pet birds that have regressed gonads. Thus, the invention also relates to a method to stimulate song in a pet bird that has regressed gonads, comprising administering to the bird an effective amount of the agent.

DETAILED DESCRIPTION OF THE PREFERRED EMBODIMENTS

Figure 1:
FIG. 1 depicts a time line showing atypical broilerization program for elite male broiler breeders, where L=light, D=dark.

The present invention relates to a method of enhancing, maintaining or stimulating the production of viable sperm in male animals and gonadal development in females. Any animal which may experience the beneficial effects of the invention may be treated according to the present invention. In general, such animals are not nocturnal and are photoperiodic. Thus, such animals must experience photoperiodic effects, e.g the elevation of blood gonadotropins and gonadal steroid levels upon the exposure to long day lengths.

In a preferred embodiment, the animal is an avian species. Alternatively, the animals are mammals, e.g. cattle, goats, sheep, horses or other veterinary animals, zoo animals, pet animals or humans.

Alternatively, the agent can be administered to stimulate the development of the female reproductive system, e.g to stimulate ovarian development.

Elite broiler breeder males, in particular, have experienced a significant decrease in reproductive performance due to their large body size. (In contrast, Leghorn males have not shown any decline in reproductive performance in recent years.) Therefore, in a preferred embodiment, the animals treated according to the present invention are elite male broiler breeders and male turkey breeders. Alternatively, the agent can treat other poultry, game bird, zoo or pet avian species that need stimulation of their reproductive system.

According to the present invention, such animals may be treated to stimulate the production of viable sperm either at an early age or at a later time, for example, after being kept in total darkness, short photoperiods, or after being fed a protein-, amino acid- or energy-deficient diet (a “marked feed-restricted” diet). In a preferred embodiment, the animals are treated with the agent and at the same time are exposed to a long photoperiod. Long photoperiods are at least LD 14:10, and preferably, LD 20:4 or greater. In contrast, short photoperiods are about 8 hours per day or less.

The light of the photoperiods may be sun light or artificially produced light. Fluorescent and incandescent light can be used. However, light which simulates the wavelength and spectrum of natural sunlight is best.

The early application of the agent may be initiated at week 1 of age and continue for about 8 to 12 weeks, preferably about 8 weeks in order to decrease generation time and obtain semen by 9–10 weeks of age (for artificial insemination of females). In a second application, the agent can be administered during the photostimulation phase (20–28 weeks) in order to synchronize the onset of puberty in males. The feed restriction phase of broilerization (weeks 8 through 20) significantly stresses the poultry. As a result, at least some of the poultry will not respond to a long day schedule of photostimulation at 20 weeks of age. Administration of the agent overcomes this problem. A third period of administration is near the end of the reproduction phase of their life cycle in order to extend and maintain reproductive productivity (week 40 and beyond).

In the case of transgenic animals, the advantage of the invention is that it decreases generation time, particularly in the male lines. Traits of interest, e.g. heterologous proteins, may therefore be expressed more rapidly in offspring and/or the eggs. Thus, the invention also relates to a method of decreasing generation time of animals, e.g. transgenic animals, and/or the time necessary to produce transgenic eggs, comprising administering to a male animal at an early time in its life, e.g. before the time that sperm is produced naturally, an effective amount of an agent which inhibits transiently the production of a thyroid hormone and stimulates gonadotropins thereby stimulating the early production of viable sperm, and artificially inseminating female animals with the sperm. Either one or both of the male and female animals may be transgenic. Optionally, transgenic eggs may be collected and the heterologous protein harvested. It normally takes 16–25 weeks to generate viable sperm in male chickens. According to the present invention, it is possible to decrease this time to 9 weeks.

In a preferred embodiment, chicks from a broiler (elite broiler breeder) male line are raised in Petersime batteries from hatch until one week of age. At one week of age, chicks are maintained on a long-day schedule (LD 20:4) or greater and fed a diet supplemented with 0.2% SMZ to stimulate the production of viable sperm. Once stimulated, the agent may be withdrawn and the long-day photoperiod schedule maintained to ensure continued production of viable sperm.

Other agents which inhibit the production in vivo of a thyroid hormone or affect their metabolism and which may be used in the practice of the present invention include, for example, compounds such as sulfonamides or pyrimidine sulfonamide derivatives, such as substituted 4-aminobenzenesulfonamides. Such compounds include the following:

U.S. Pat. No. 3,214,335 discloses 2-sulfanilamido-5-alkoxypyrimidines.

U.S. Pat. No. 2,240,496 discloses substituted N-(p-aminobenzene-sulfonyl)benzamide.

U.S. Pat. No. 2,411,495 discloses 4-aminobenzenesulfonacetyl amides.

U.S. Pat. No. 2,790,798 discloses substituted 4-aminobenzenesulfonamides of the formula:

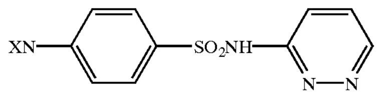

wherein X is an alkanoyl group.

U.S. Pat. No. 3,375,247 discloses substituted 4-aminobenzenesulfonamides of the formula:

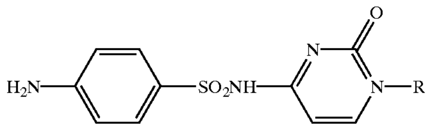

wherein R is lower alkyl, lower alkoxyalkyl, lower alkenyl or phenyl-substituted lower alkyl.

U.S. Pat. No. 2,417,005 discloses p-aminobenzene sulfone $N^1$-acetylamides.

U.S. Pat. No. 3,127,398 discloses substituted sulfonamides of the formula:

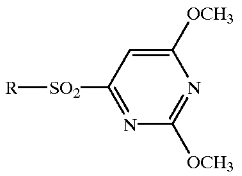

where R is lower alkyl, phenyl lower alkyl, phenyl, naphthyl, lower alkanoylaminophenyl, hydroxy and OMe, wherein Me represents a metal atom selected from the group consisting of alkali metal and alkaline earth metal.

U.S. Pat. No. 3,132,139 discloses substituted 4-aminobenzenesulfonamides of the formula:

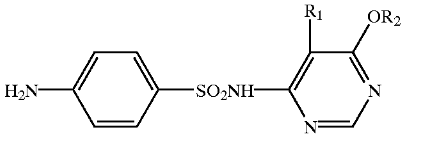

wherein $R_1$ and $R_2$ are lower alkyl groups or $R_1$ is H or $OR_2$.

U.S. Pat. No. 2,218,490 discloses N-(p-aminobenzenesulfonyl)-benzamide.

U.S. Pat. No. 3,562,258 discloses $N^1$-[p-aminobenzenesulfonyl]-$N^3$-[4,5-dimethyloxazolyl-(2)] guanidine.

U.S. Pat. No. 3,098,069 discloses substituted 4-aminobenzenesulfonamides of the formula:

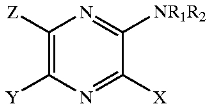

wherein

X is $OCH_3$ or $OC_2H_5$;

Y is H, Br or lower alkyl;

Z is H or lower alkyl;

$R_1$ is H or lower alkyl; and $R_2$ is a member of the group consisting of:

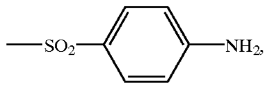

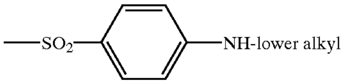 and

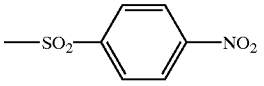

U.S. Pat. No. 2,888,455 discloses 3-sulfanilamido-5-methylisoxazole.

U.S. Pat. No. 2,712,012 discloses substituted 4-aminobenzenesulfonamides of the formula:

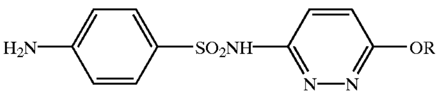

wherein R is an alkyl, aralkyl or aryl radical.

U.S. Pat. No. 4,151,164 discloses 3-methoxy-4-(4'-aminobenzenesulfonamido)-1,2,5-thiadiazole.

Preferred compounds which inhibit thyroid hormone synthesis or reduce levels of thyroid hormones (due to altered metabolism) include methimazole, thiourea, propylthiouracil, thiouracil, carbimazole, thiobarbital, and ionic inhibitors such as thiocyanate and perchlorate. Other preferred compounds include sulfathiazole, sulfaethoxypyridazine, acetyl sulfamethoxypyridazine, sulfachloro-pyrazine, mafenide, sulfisoxazole. succinylsulfathiazole, phthalylsulfathiazole, trimethoprim, sulfanilylguanidine, sulfanilamide, sulfadimindine, sulfamethylphenazole, sulfaquinoxaline, sulfapyridine, sulfapyrazine, sulfabenz, sulfabenzamide, sulfabromethazine, sulfacetamide, sulfachlorpyridazine, sulfachrysoidine, sulfacytine, sulfadiazine, sulfadicramide, sulfadimethoxine, sulfadoxine sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyridazine, sulfamethylthiazole, sulfametrole, ethylenethiourea, resorcinol and the aminoglycoside netilmicin (du Souich, P. et al., *Clin. Pharmacol. Ther.* 38:686–691 (1985)).

The agent may be administered to the animal in any means which achieves the intended purpose. For example, the agent may be administered by oral, intravenous, intramuscular, buccal, intranasal, rectal, or other means together with an acceptable carrier. In a preferred embodiment, the agent is administered to the animal as part of its food or water. In the case of humans, it is preferred that the agent be administered orally.

The dosage administered will be dependent upon the type of animal as well as the age, health, and weight, the kind of concurrent treatment, if any, frequency of treatment, and the nature of the effect desired. When the agent is administered as part of the food of a male broiler breeder, a preferred concentration is between about 0.1% to no more than 0.3% of the feed. In a most preferred embodiment, the agent is sulfamethazine added at a concentration of about 0.2%.

The compositions of the invention may comprise the agent at a unit dose level of about 50 to about 600 mg/kg of body weight per day, or an equivalent amount of the pharmaceutically acceptable salt thereof, on a regimen of 1–4 times per day.

In addition to administering the compound as a raw chemical, the agent may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

The agents may be administered as a non-toxic pharmaceutically acceptable salt. Acid addition salts are formed by mixing a solution of the particular agent with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the particular agent with a solution of a pharmaceutically acceptable non-toxic base such as sodium hydroxide, potassium hydroxide, choline hydroxide, sodium carbonate and the like.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the agent the form of granules which may be mixed with fillers such as lactose, binders such as starches, and/or lubricants such as talc or magnesium stearate and, optionally, stabilizers. In soft capsules, the agents are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the agents with a suppository base. Suitable suppository bases are, for example, natural or synthetic triglycerides, or paraffin hydrocarbons. In addition, it is also possible to use gelatin rectal capsules which consist of a combination of the agents with a base. Possible base materials include, for example, liquid triglycerides, polyethylene glycols, or paraffin hydrocarbons.

Suitable formulations for parenteral administration include aqueous solutions of the agents in water-soluble form, for example, water-soluble salts and alkaline solutions. In addition, suspensions of the agents as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and animal husbandry which are obvious to those skilled in the art are within the spirit and scope of the invention.

EXAMPLES

Figure 2:
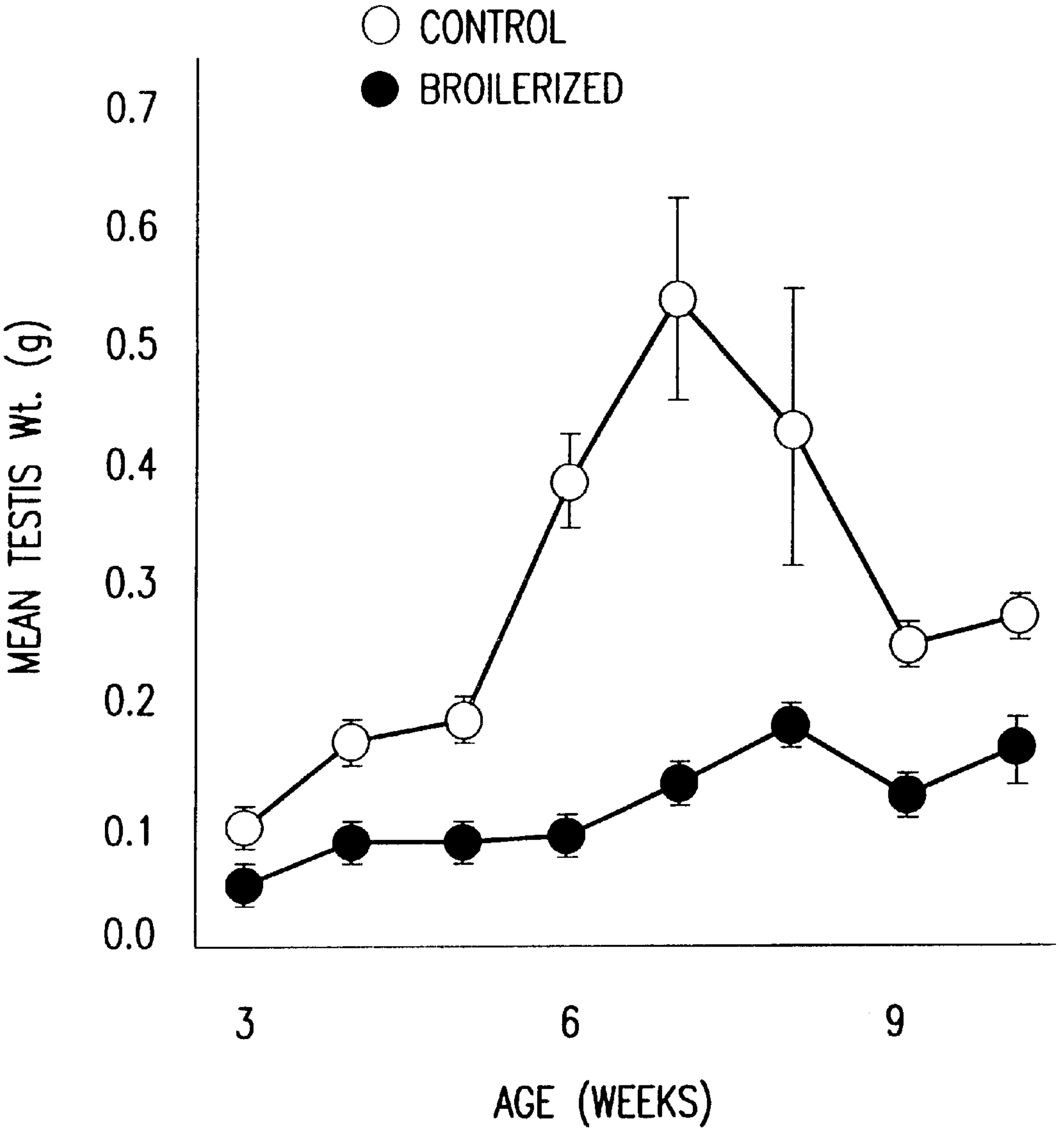
FIG. 2 depicts a graph showing the effect of the "metabolic" or feed restriction phase of broilerization on testis development.
Figure 3:
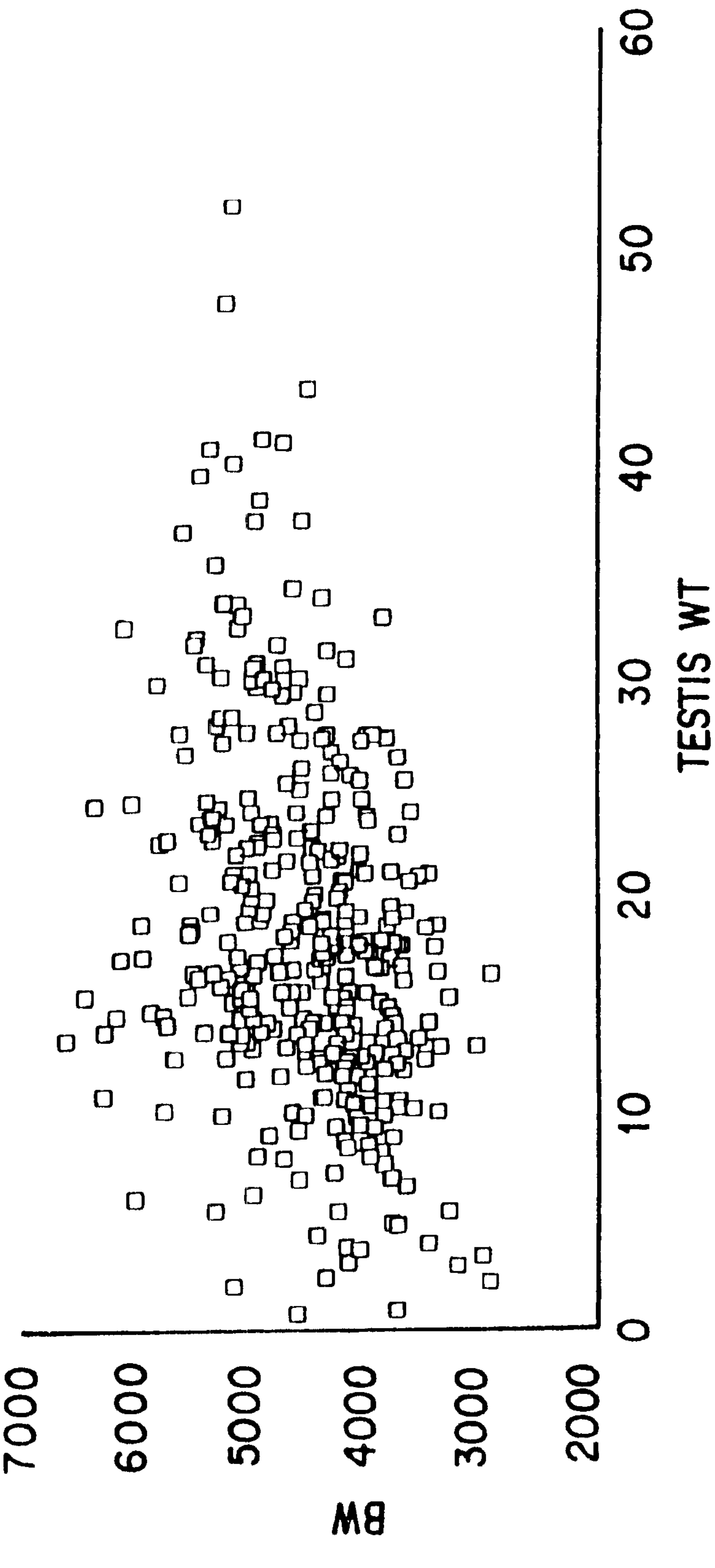
FIG. 3 depicts a graph showing the effects on both the "metabolic" and "photoperiodic" phases of broilerization on testis size, where BW=body weight (sampled from weeks 28–50).

A management program may be employed for elite male broiler breeders (grandparent and great-grandparent stock) in order to enable geneticists to select parents for the next generation, raise them to maintain a body weight that closely matches an optimized growth curve to prevent obesity, and finally subject birds to long-day photostimulation in order to maintain their reproductive productivity throughout their adult life. The term 'broilerization' has been used to describe this management process. FIG. 1 shows a typical broilerization program for male breeders. This program is divided into three phases: the Genetic Selection Phase, Metabolic or Feed Restriction Phase and Photoperiodic/ Photostimulation Phase. The first phase incorporates a long photoperiod, and high protein/high energy starter diet in order to stimulate growth rate thereby aiding parent stock selection for the next generation. Thereafter a significantly reduced photoperiod coupled with rigorous dietary restriction is implemented to manage weight gain. This stage is referred to as the "Metabolic" Phase. Finally, birds are subjected to an increased photoperiod ("Photoperiodic" Phase) with some feed restriction to stimulate and maintain reproductive performance throughout the remainder of their life cycle. It is clear that the latter two phases of the management program are distinct and hence need to be examined separately in order to understand better the complete reproductive cycle of modern elite broiler breeders. FIG. 2 illustrates how the "Metabolic" Phase compromises testes development of broilerized males. Note that the first seven weeks of feed ad libitum and long photoperiod result in stimulation of testes development. However, upon entry into the metabolic phase, severe restricted food intake and a short photoperiod (Light/Dark, LD8:16) result in a marked decline in testes size such that the gain made in testes development during the initial genetic selection phase, is lost by the end of the metabolic phase. When one examines the results of testes development obtained from a small population of elite broiler breeders using the recommended, present-day management system, much variability in testis size is seen (FIG. 3). The heterogeneous response of the testes suggests that a large proportion of the population may never develop fully functional testes.

Figure 4:
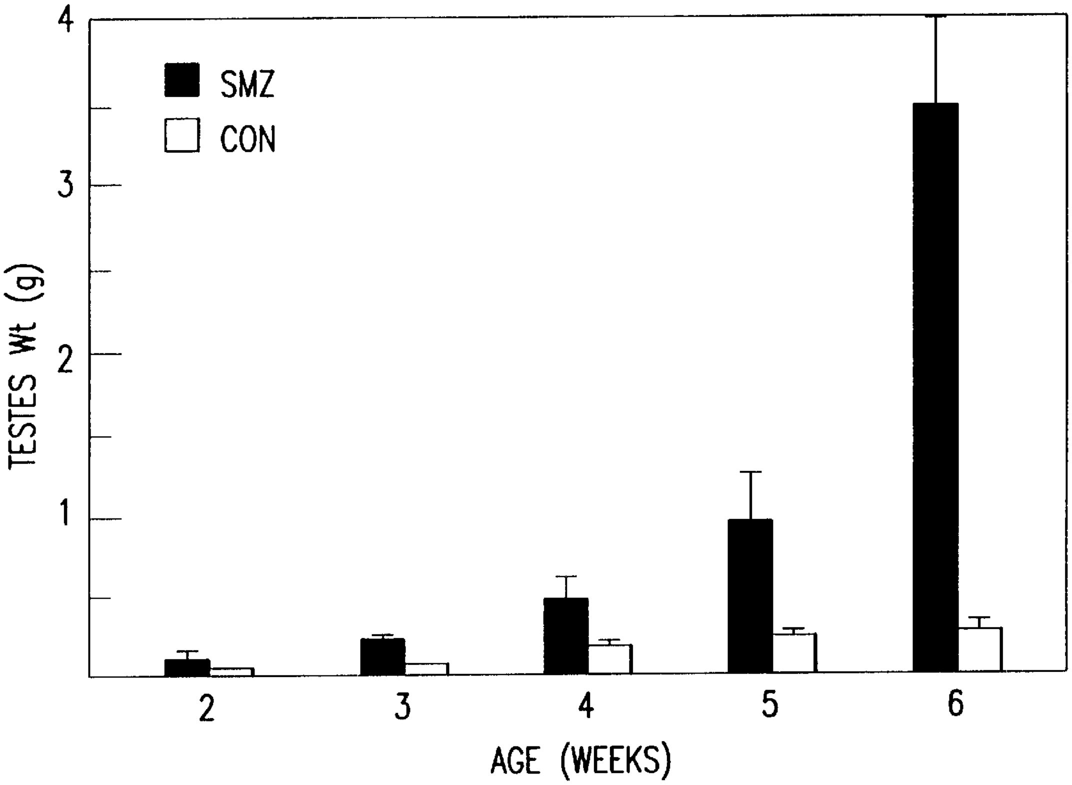
FIG. 4 depicts a bar graph showing the testes response resulting from the "genetic selection" phase of broilerization (see FIG. 1) plus 0.2% sulfamethazine (SMZ) added to a standard starter ration at one week of age.
Figure 5A:
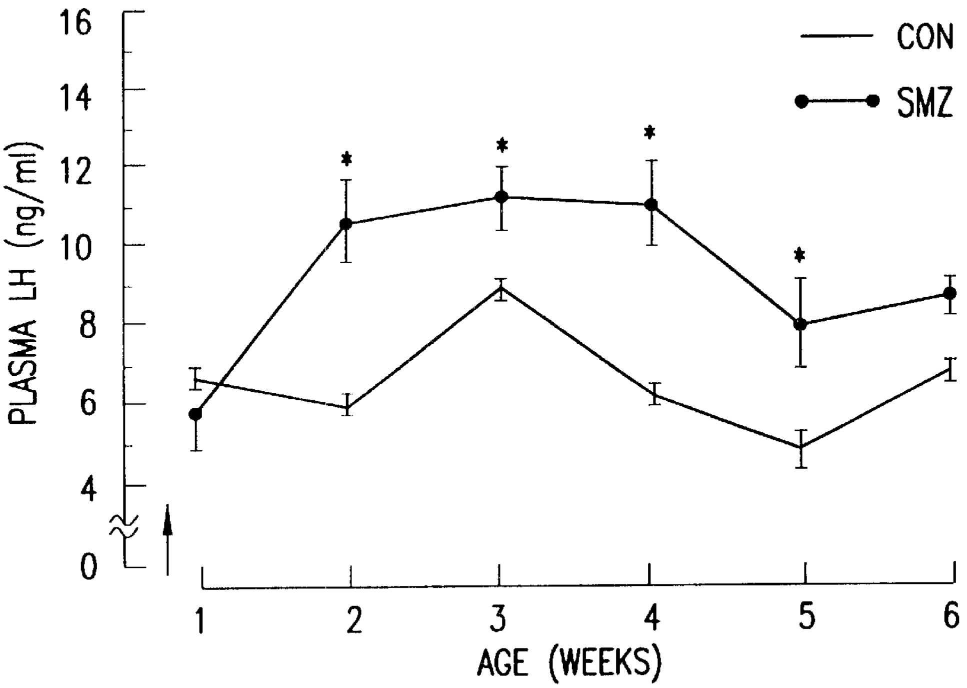
FIGS. 5A and 5B depict graphs showing weekly levels of plasma luteinizing hormone (LH; 5A) and follicle stimulating hormone (FSH; 5B) in male broiler chicks fed a diet with 0.2% SMZ beginning at one week of age (*=p>0.05).
Figure 5B:
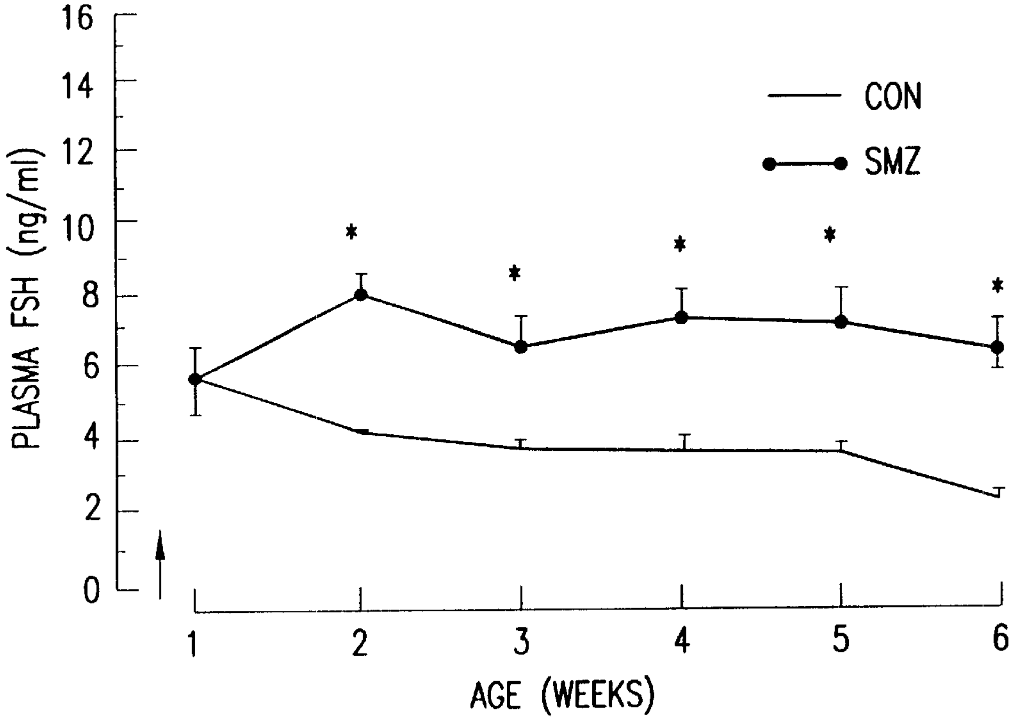
Figure 6:
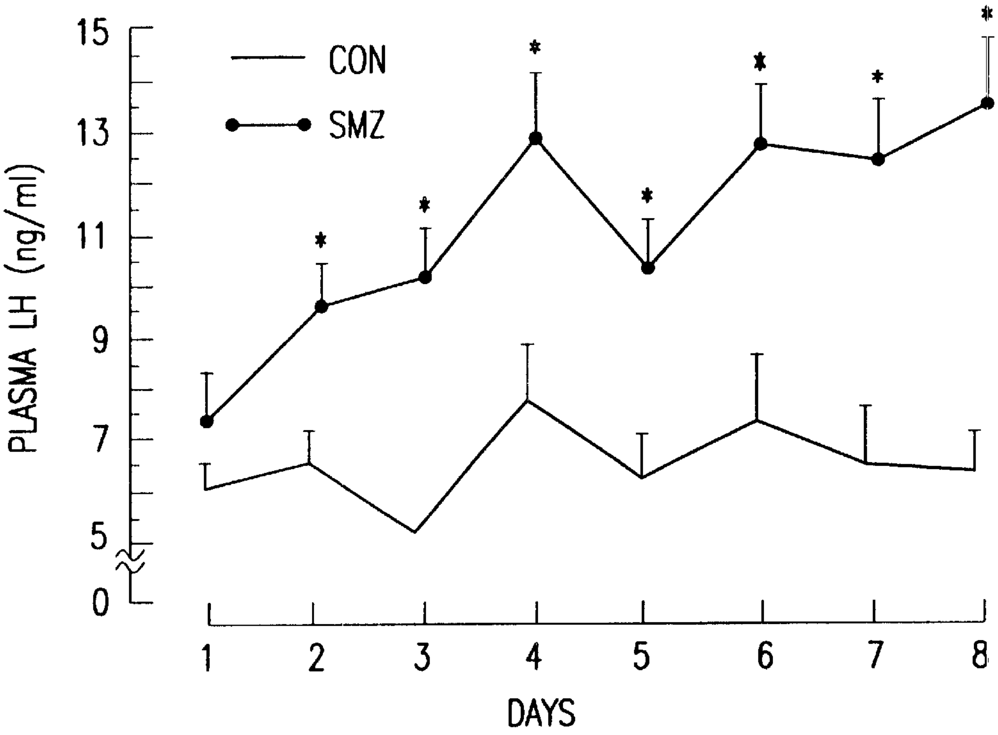
FIG. 6 depicts a graph showing daily levels of LH immediately following dietary administration of 0.2% SMZ, beginning at one week of age (*=p<0.05).

FIG. 4 shows the testes response resulting from giving a starter ration supplemented with 0.2% SMZ during the genetic selection phase of broilerization. The compound significantly increased the rate of testes growth and by nine weeks of age, broiler chicks produced viable semen. Blood samples were taken starting at day of SMZ administration and weekly following initiation of the treatment. Both luteinizing hormone (LH, FIG. 5A) and follicle stimulating hormone (FSH, FIG. 5B) were significantly increased. To establish how rapidly LH rises following SMZ intake, a second study showed that plasma LH was significantly elevated within 48 hr. of consuming feed containing SMZ (FIG. 6).

Figure 7A:
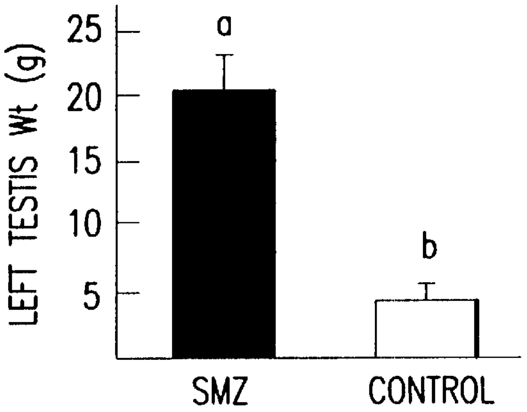
FIGS. 7A and 7B depict bar graphs showing testis weight response (7A) and plasma LH (7B) resulting from the "photoperiodic" phase of broilerization plus 0.2% SMZ added to a grower diet from 20 to 28 weeks of age. Testes and blood were sampled at 28 weeks of age. Photoperiod=LD 14:10.
Figure 7B:
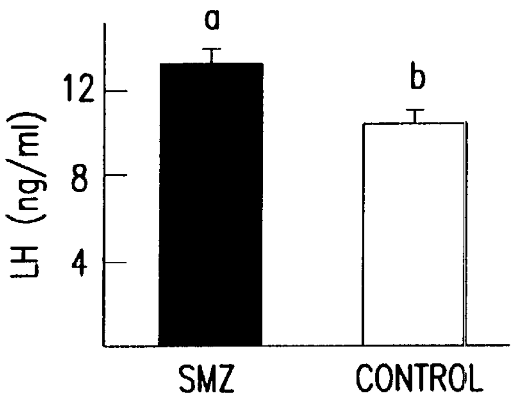
Figure 8A:
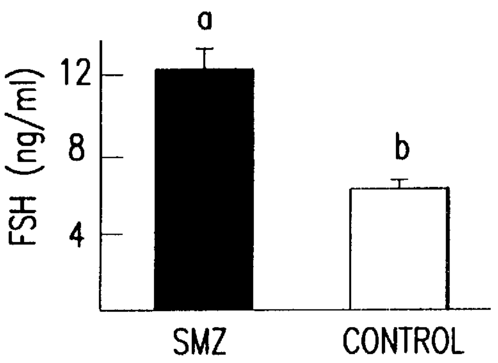
FIGS. 8A and 8B show plasma FSH (8A) and testosterone (8B) resulting from blood samples taken as described with respect to FIGS. 7A and 7B.
Figure 8B:
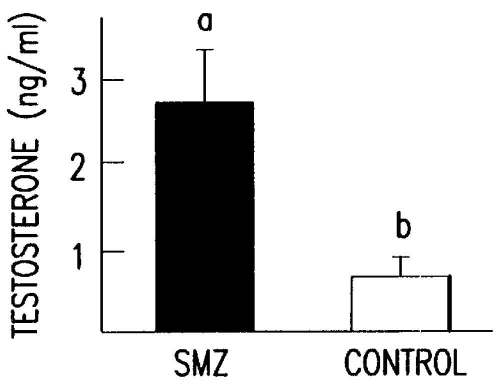

Sulfamethazine was also administered during the photoperiodic phase (LD 14:10) of broilerization (Weeks 20–28) and similar to the results obtained with one week old chicks, testis weight (FIG. 7A) of treated broiler breeders was significantly heavier than controls ($p \leqq 0.05$). Blood samples were taken at week 28 and LH (FIG. 7B), FSH (FIG. 8A) and testosterone (FIG. 8B) were all significantly elevated ($p \leqq 0.05$). Hence, SMZ can be administered at either a young age or near sexual maturity and development of the male gonadal system is stimulated.

Figure 9:
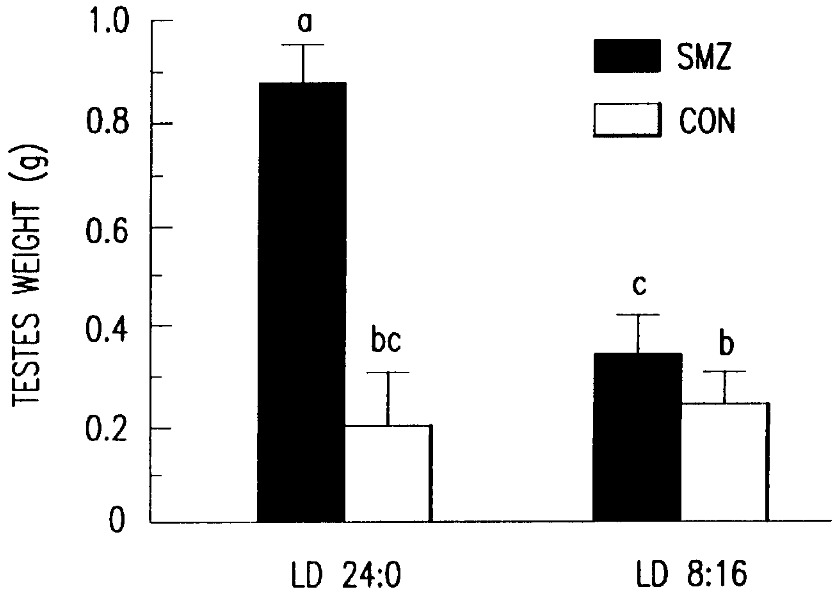
FIG. 9 depicts a bar graph showing testes weight following 0.2% SMZ (1–4 weeks of age) in chicks exposed to LD 24:0 or LD 8:16.

In a further study using broiler chicks, SMZ at 0.2% was added to a standard broiler ration and fed to chicks from one to four weeks of age. One group was raised under continuous light while a second group was exposed to a photoperiod of LD 8:16. Results are shown in FIG. 9. Chicks which consumed SMZ and were exposed to continuous light had significantly elevated testes growth ($p \leqq 0.05$). In contrast, the progonadal effects of SMZ were markedly attenuated in chicks housed under a short photoperiod. Although food intake was not measured in this experiment, body weight was taken at the beginning and end of the study. No significant difference in body weight was observed between long-day and short-day SMZ treated groups, suggesting that intake of feed, and therefore SMZ, was not different between the two experimental groups. Sulfamethazine has a stimulatory effect upon testes growth when chicks are exposed to a long photoperiod. One possible interpretation is that SMZ appears to facilitate or amplify the stimulatory effect of long-day light on gonadal development in male chicks.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims.

All publications, patents and patent applications mentioned in this specification are indicative of the level of skill of those in the art to which the invention pertains. All publications, patents and patent applications are herein incorporated by reference to the same extent as if each individual publication or patent application was specifically and individually indicated to be incorporated by reference in their entirety.

What is claimed is:

1. A method for enhancing the development of sperm in a male avian species, and maintaining thereafter the production of sperm, comprising (a) administering to said avian species an effective amount of a sulfonamide which inhibits the production of thyroid hormone and stimulates gonadotropins and exposing said avian species to a long photoperiod for a time sufficient to stimulate production of sperm; wherein the long photoperiod is at least LD 14:10, and the time is at least 9 weeks, then (b) withdrawing administration of sulfonamide and continuing exposure of said avian species to a long photoperiod to maintain production of sperm.

2. The method of claim 1, wherein said avian species is a chicken.

3. The method of claim 1, wherein said sulfonamide is selected from the group consisting of sulfathiazole, sulfaethoxypyridazine, acetyl sulfamethoxypyridazine, sulfachloro-pyrazine, sulfisoxazole, succinylsulfathiazole, phthalylsulfathiazole, sulfanilylguanidine, sulfanilamide, sulfadimindine, sulfamethylphenazole, sulfaquinoxaline, sulfapyridine, sulfapyrazine, sulfabenz, sulfabenzamide, sulfabromethazine, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanole, sulfalene, sulfaloxic acid, sulfamerazine, sulfameter, sulfamethazine, sulfamethizole, sulfamethomidine, sulfamethoxazole, sulfamethoxypyridazine, sulfamethylthiazole and sulfametrole.

4. The method of claim 1, wherein said sulfonamide is sulfamethazine.

5. The method of claim 1, wherein said sulfonamide is administered to said avian species as part of its food.

6. The method of claim 5, wherein said sulfonamide is present at 0.2% in said food.

7. The method of claim 1, wherein said long photoperiod is at least LD 20:4.

8. The method of claim 1, wherein said administering and exposing in (a) occurs from 1 week of age to 12 weeks of age.

9. The method of claim 1, wherein said administering and exposing in (a) occurs from 1 week of age to 10 weeks of age.

10. The method of claim 1, further comprising administering a sulfonamide to said avian species prior to the collapse of its reproductive system to extend and maintain the production of sperm and reproductive productivity.

11. The method of claim 10, wherein said administering a sulfonamide to maintain the production of sperm and reproductive productivity occurs at 40 weeks of age and beyond.

12. The method of claim 10, wherein said sulfonamide is administered to said avian species as part of its food at 0.2%.

13. The method of claim 10, wherein said sulfonamide administered to said avian species prior to collapse of its reproductive system is sulfamethazine.

14. A method for enhancing the development of sperm in a male chicken and maintaining thereafter the production of sperm, comprising (a) administering to said chicken as part of its food an effective amount of sulfamethazine and exposing said chicken to a long photoperiod of at least LD 14:10 for a time sufficient to stimulate production of sperm; wherein the time is at least 9 weeks, then (b) withdrawing sulfamethazine from the food of the chicken and continuing exposure of the chicken to said long photoperiod to maintain production of sperm.

15. The method of claim 14, where said long photoperiod is at least LD 20:4 and said administering and exposing in (a) occurs from 1 week of age to 12 weeks of age.

16. The method of claim 14, where said long photoperiod is at least LD 20:4 and said administering and exposing in (a) occurs from 1 week of age to 10 weeks of age.

17. The method of claim 14, where said long photoperiod is at least LD 20:4 and said administering and exposing in (a) from 1 week of age to 9 weeks of age.

18. The method of claim 14, further comprising administering an effective amount of said sulfamethazine to said chicken at 40 weeks of age and beyond to maintain the production of sperm and reproductive productivity.

* * * * *